(12) United States Patent
Birmingham

(10) Patent No.: US 6,299,587 B1
(45) Date of Patent: Oct. 9, 2001

(54) ANKLE-FOOT ORTHOSIS AND METHOD

(76) Inventor: William W. Birmingham, 2108 Popular, Victoria, TX (US) 77901-4326

(*) Notice: Subject to any disclaimer, the term of this patent is extended or adjusted under 35 U.S.C. 154(b) by 0 days.

(21) Appl. No.: 09/729,407

(22) Filed: Dec. 4, 2000

Related U.S. Application Data

(63) Continuation of application No. 09/591,233, filed on Jun. 8, 2000.

(51) Int. Cl.⁷ ..................................................... A61F 5/00
(52) U.S. Cl. .................................. 602/5; 602/23; 602/26
(58) Field of Search .............................. 128/869, 882; 602/5, 23, 24, 27, 28, 29

(56) References Cited

U.S. PATENT DOCUMENTS

| | | |
|---|---|---|
| 6,214 | 3/1849 | Yerger . |
| 106,907 | 8/1870 | Wood . |
| 453,475 | 6/1891 | Harding . |
| 839,223 | 12/1906 | Stevens . |
| 1,332,047 | 2/1920 | Lasher . |
| 1,336,001 | 4/1920 | Tranmer . |
| 1,356,327 | 10/1920 | Winiarski . |
| 1,381,290 | 6/1921 | Diadul . |
| 2,516,872 | 8/1950 | Hauser et al. . |
| 2,973,757 | 3/1961 | Katthoefer . |
| 3,086,521 | 4/1963 | Desai et al. . |
| 4,459,980 | 7/1984 | Perser et al. . |
| 4,510,701 | 4/1985 | Schour et al. . |
| 4,936,295 | 6/1990 | Crane . |
| 5,184,275 | 2/1993 | Wiegel et al. . |
| 5,672,156 | 9/1997 | Ramos . |

Primary Examiner—Michael A. Brown
(74) Attorney, Agent, or Firm—Robert H. Johnston

(57) ABSTRACT

An ankle-foot orthosis (A.F.O.) has an upper post for securing to a patient's leg, a shoe with an exterior surface on the heel, and a shoe-attachment device that attaches to the shoe and pivotably couples to the upper post member. A first shoe attachment device has a u-shaped member that is angled inward to be substantially co-planar with the exterior angled surface of the shoe to engage it and that has attachment posts that pivotably connect to the upper post. It also has an edge that engages the shoe. A second shoe attachment device is a u-shaped member having channel-and-hook connection on each end that is operable to receive and hold a fastener that extends through a channel in the heel of the shoe. It may also have a convex portion that mates with a trough on the shoe. Methods of manufacturing these types of systems are also presented.

3 Claims, 4 Drawing Sheets

ANKLE-FOOT ORTHOSIS AND METHOD

This is a continuation of copending application Ser. No. 09/591,233, filed on Jun. 8, 2000.

TECHNICAL FIELD OF THE INVENTION

The present invention relates to orthosis devices, and more particularly, to an ankle-foot orthosis (A.F.O.) and method.

BACKGROUND OF THE INVENTION

Ankle-foot orthosis are used to control the alignment and motions of the joints of the foot and ankle of a patient. In a conventional arrangement, the AFO is constructed of metal and plastic usually consisting of two metal uprights or posts whose proximal ends are connected to a leather-covered metal or plastic calf bands and whose distal ends are the proximal part of the ankle joint mechanism. The shoe or foot attachment completes the mechanical ankle and anchors the orthosis distally. Primarily three types of shoe attachment devices have been used: stirrups, calipers, or shoe inserts.

Stirrups involve usually a solid, steel stirrup that is riveted directly to the sole of the shoe under the anterior section of the heel. The stirrup surrounds the heel and has a member going underneath the heel attached to it with fasteners.

A caliper involves a round tube placed in the heel of the shoe that receives the caliper for attachment. The caliper allows for interchangeability of shoes compared to the stirrups that are riveted. The draw-back of this design is that the pivot of the mechanical joint is typically at the level of the shoe heel.

With a shoe insert, a stirrup-like arrangement is essentially incorporated into the interior of the shoe and is shaped to contour to the patient's foot that fits into the shoe. Considerable time and skill are required to fabricate a proper insert of this type. Further, a larger shoe is typically required to accommodate the insert.

Between the shoe attachments and the metal upright posts is the ankle joint mechanism. These joint mechanisms are frequently single-axis joints that control mediolateral motion by stopping or blocking it and dorsiflexion and plantar flexion by means by stops or assists. The stops limit the movement and may be placed as a plantar-flexion (posterior) stop and/or a dorsiflexion (anterior) stop. The assists are usually springs that aid motion. With a dorsiflexion assist (anterior), the spring is compressed after heel strikes which helps to control plantar flexion.

Concerning the uprights or posts in the calf bands, historically the most frequently used have been the tube post design, but a single bar brace can be used in cases of relatively mild dorsiflexion weakness. Further, with molded plastic designs, a molded calf shell may be desirable that surrounds a substantial portion of the posterior portion of a patient's lower leg.

While developed systems have provided assistance to patients, there are a number of shortcomings. For example, conventional designs of AFOs do not allow for use with a patient's existing shoes and do not allow for easy removal without including bulky attachments.

SUMMARY OF THE INVENTION

Therefore, a need has arisen for an ankle-foot orthosis and method that address shortcomings of previous systems and methods. According to an aspect of the present invention, an ankle-foot orthosis has an upper post for securing to a patient's leg, a shoe with an exterior angled surface on the heel, and a shoe-attachment device that attaches to the shoe and pivotably couples to the upper post member, and wherein the shoe attachment device has a u-shaped member that is angled inward to be substantially co-planar with the exterior angled surface of the shoe to engage it and that has attachment posts that pivotably connect to the upper cost. According to a more specific aspect of the present invention, a strap may be included to help further wedge a portion of the u-shaped member against a lip portion of the shoe.

According to another aspect of the present invention, an ankle-foot orthosis system has an upper post for securing to a patient's leg, a shoe with a heel having a lateral channel through it, and a shoe-attachment device that attaches to the shoe and pivotably couples to the upper post member, and wherein the shoe attachment device is a u-shaped member having channel-and-hook connection on each end that is operable to receive and hold a fastener that extends through the channel in the heel of the shoe and also having attachment posts that are used to pivotably connect to the upper post. The channel-and-hook connection holds the u-shaped member in tension about the heel. According to a more specific aspect of the invention, the shoe may also have a trough portion that mates with a convex portion formed on the u-shaped member of the attachment device.

According to another aspect of the present invention, a method for manufacturing an AFO system includes the steps of providing an upper post for attaching to a patient's calf; attaching a calf connection strap to the upper post member; providing a shoe having an exterior angled heel portion; and providing a shoe attachment device, wherein providing the shoe attachment device involves forming an angled, u-shaped member having an interior surface that is substantially co-planar with an exterior angled surface of the heel of the shoe when the attachment device is placed on the shoe and an edge that engages the shoe, attaching attachment posts to the u-shaped members and pivotably attaching the attachment posts to the upper post.

According to another aspect of the present invention, a method for manufacturing an ankle foot orthosis system includes the steps of providing an upper post member for attaching to a patient's calf; attaching a releasable calf connection strap to the upper post member; pivotably coupling an attachment device to the upper post member; wherein the attachment device includes a u-shaped member having a first channel-and-hook connection and a second channel-and-hook connection, each channel-and-hook connection operable to receive and engage a flanged fastener head, first and second attachment posts coupled to the u-shaped member; and wherein the attachment device is attached to the shoe by placing a fastener (that has flanged heads on each end) laterally through the heel of the shoe with the flanged heads extending on opposite sides of the heel and engaging the first and second channel-and-hook connections.

The present invention provides advantages; a number of examples follow. An advantage of the present invention is that it provides an easily applied AFO that a patient should be able to attach themselves. Another advantage of the present invention is that the AFO may be attached quickly. Yet another advantage is that the AFO system of the present invention is relatively light weight. According to yet another advantage, a patient may use their regular size shoe—i.e., they do not have to obtain a larger size shoe.

BRIEF DESCRIPTION OF THE DRAWINGS

For a more complete understanding of the present invention and advantages thereof, reference is now made to the following description taken in conjunction with the accompanying drawings in which like reference numbers indicate like features, and wherein.

DETAILED DESCRIPTION OF THE INVENTION

Figure 1:
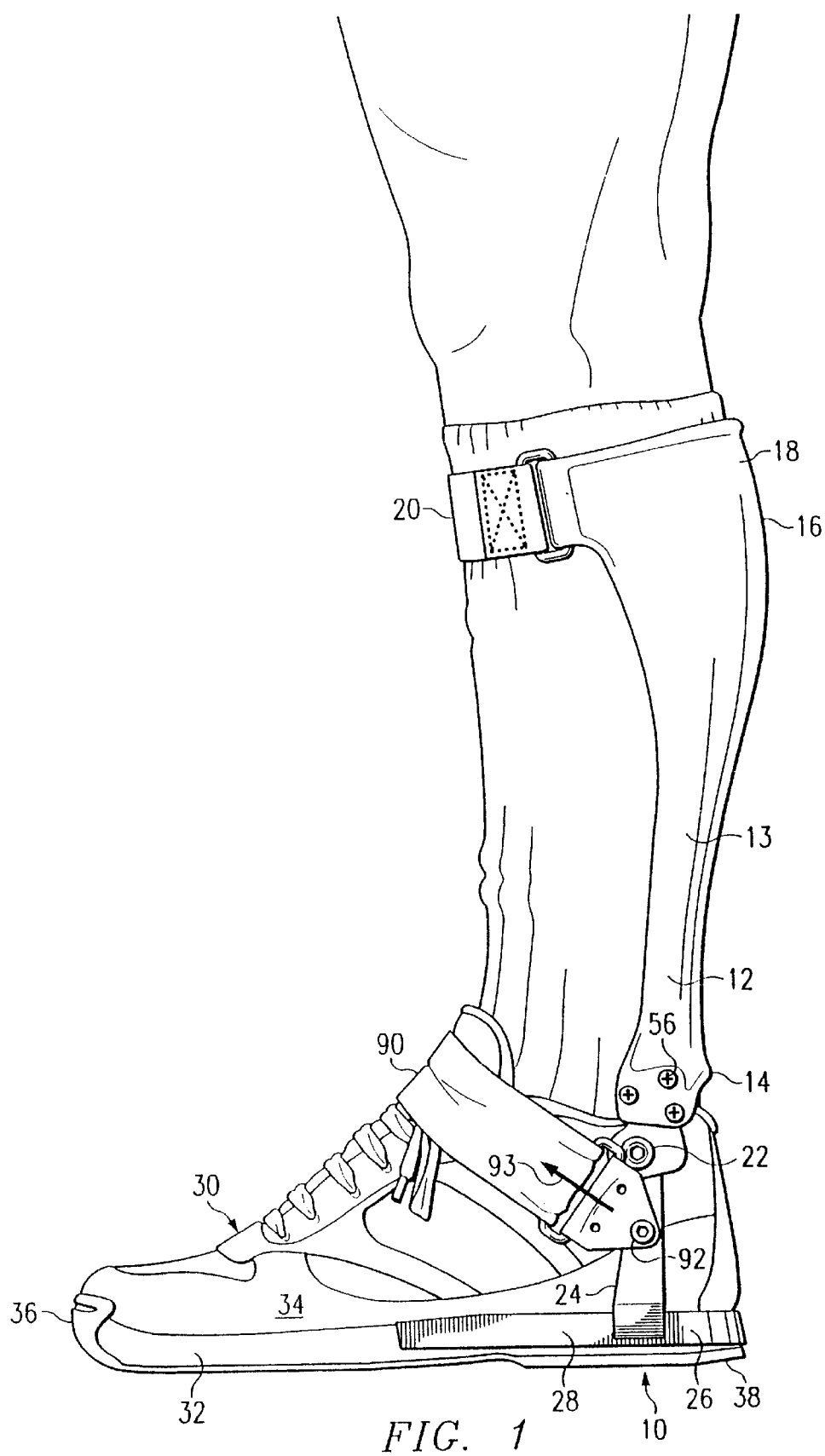
FIG. 1 is a side elevational skematic of an ankle-foot orthosis according to an aspect of the present invention being used by a patient.

The preferred embodiment of the present invention and its advantages are best understood by referring to FIGS. 1–7 of the drawings, like numerals being used for like and corresponding parts of the various drawings.

Referring to FIGS. 1–4, an ankle-foot orthosis system 10 has an upper post member 12 having a first end 14 and a second end 16. Post member 12 is formed as a single member with calf shell 13. A calf band 18 is attached to second end 16 of upper post 12 or formed as a contiguous part of it. The calf band 18 has a selectively detachable calf strap 20 secured to two portions of it such that the calf band 18 may be held snugly against a lower portion of a patient's leg. The selectively detachable strap 20 is preferably a hook-and-loop attachment strap, e.g. Velcro®.

Figure 2:
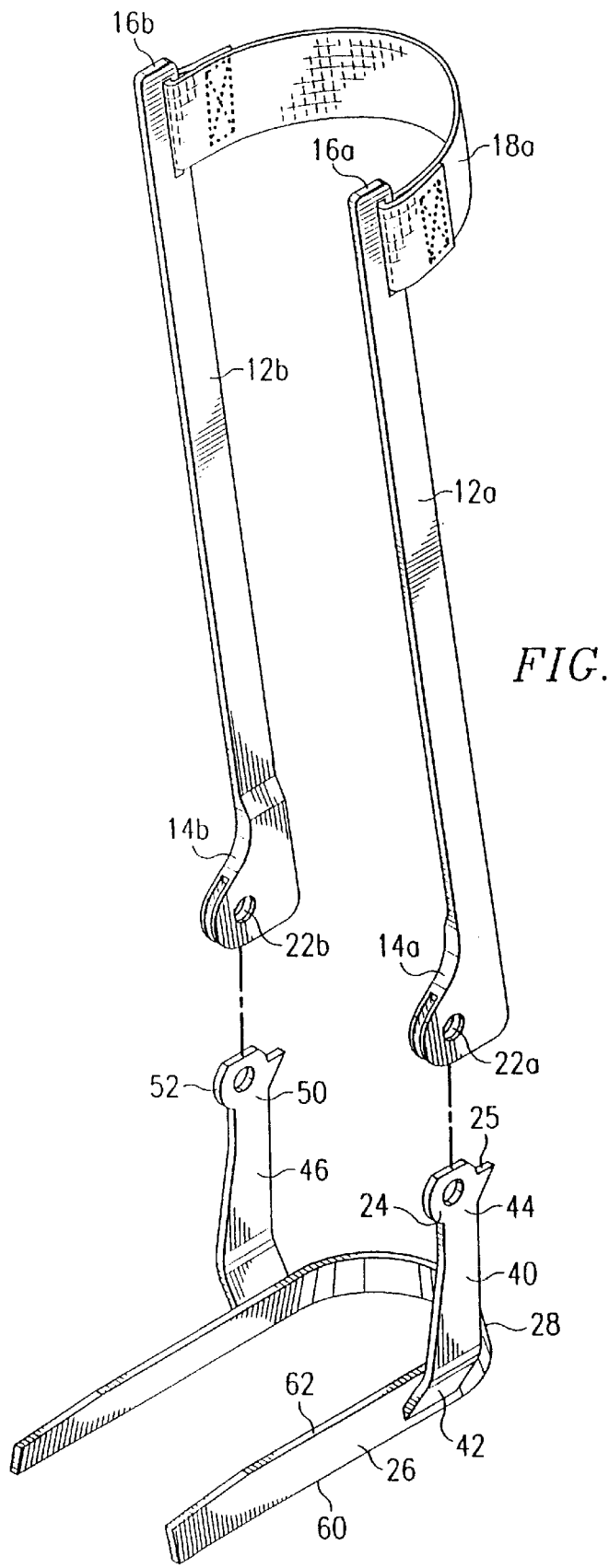
FIG. 2 is a perspective view of the attachment device 26 of FIG. 1 shown in an exploded view but with an alternative embodiment of the post member (12a 12b)

Referring to FIG. 2, the system is the same as that shown in FIG. 1, but an alternative post is presented. The alternative post member is formed by two posts 12a, 12b. The post 12a, 12b have calf band 18a secured to their second ends 16a, 16b, respectively. Pivot connection members 22a, 22b are attached to the first ends 14a, 14b, respectively.

Returning primarily to FIG. 1, formed on first end 14 of upper post member 12 or attached to it is a pivot connection member 22. Pivot connection member 22 releasably and pivotally connects with a cooperating pivot connection member 24 (see FIG. 2) formed on a portion of an attachment device 26. The attachment device 26 has a U-shaped member 28 which in this embodiment is angled as will be described in more detail below. The U-shaped member 28 is sized and configured to attach to shoe 30.

The shoe 30 has a sole sidewall 32, an outer shoe surface or portion 34, a front portion 36, and a heel 38. As will be described further below, sole sidewall 32 has an angle with respect to a vertical reference near the heel portion 38.

As shown best in FIG. 2, attachment device 26 has a first attachment post 40 having a first end 42 and a second end 44. The first end 42 is attached to the U-shaped member 28. The attachment post member 40 has pivot connection member 24 formed or attached on second end 44 and similarly, a second post member 46 has pivotal connection member 52 formed on second end 50. The pivotable connection members 24 and 52 cooperate with pivot connection members 22a, 22b of the upper post member 12 to form a releasable, pivotable connection between attachment device 26 and upper post member 12. Connection members 24 and 52 may include stops 25 to limit the pivotable motion. The pivot may include other components such as pins and fasteners not explicitly shown but known in the art. As shown in FIG. 1, if upper post member 12 is formed of plastic material, it may be desirable to use a metal pivot connection 22 that is attached to first end 14 of the upper post member 12 by fasteners 56.

Figure 3:
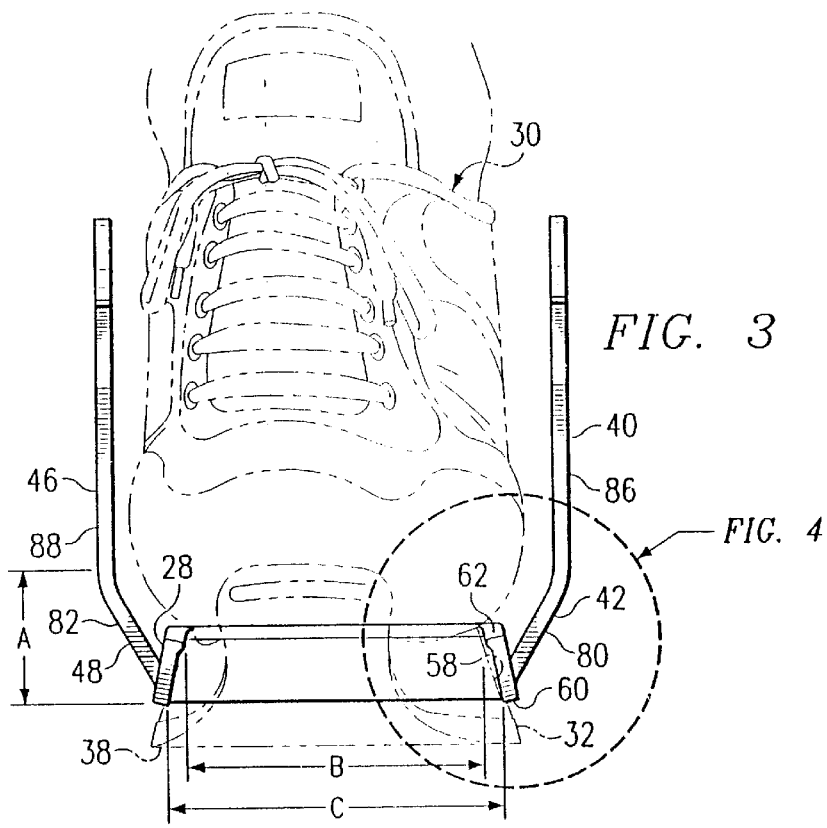
FIG. 3 is a front elevational view of the attachment member of FIGS. 1 and 2.
Figure 4:
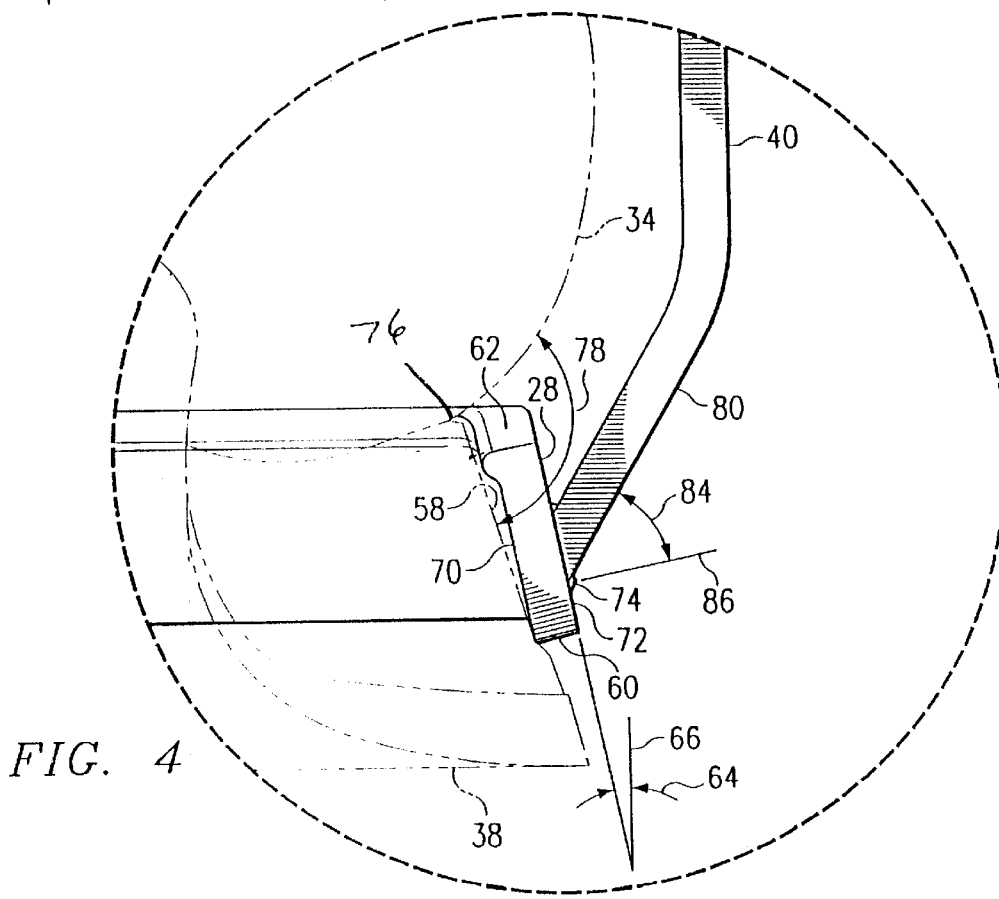
FIG. 4 is a detailed elevation view of a portion of the attachment device shown in FIG. 3.

As shown best in FIGS. 3 and 4, shoe 30 is formed with an exterior angled surface 58. The U-shaped member 28 has a first edge 60 and a second edge 62, and a U-shaped member 28 is angled such that second edge 62 is more inward than first edge 60 with respect to the interior of the U-shaped. As shown best in FIG. 4, this means that U-shaped member 28 forms an angle 64 with respect to a vertical reference line 66. Angled 64 is formed to substantially match the angle of the exterior angled surface 58. By angled to match, it is meant that the interior surface 70 of U-shaped member 28 is substantially coplanar with the exterior angled surface 58 of shoe 30. By being substantially coplanar, it is meant that preferably at least 10 percent of the surfaces engage each other and more preferably greater than 25 percent and more preferably still greater than fifty percent. The attachment posts 40, 46 are attached on an exterior surface 72 of U-shaped member 28 by any means known in the art but is preferably by a welded connection such as welded connections 74 (FIG. 4). The posts 40, 46 are preferably mounted to U-shaped member 28 substantially aligned with each other.

The shoe 30 preferably has a lip 76 formed at the junction between the outer shoe portion 34 and the angled sidewall 58. This lip 76 is formed by an angled 78. It is preferable that second edge 62 of the U-shaped member 28 be wedged into the crevice at lip 76. Near first ends 42, 48 of posts 40, 46, respectively, are first linear portions 80, 82 which form an angle 84 with respect to reference line 86 which is perpendicular to the exterior surface 72 of U-shaped member 28. Angle 84 may range between 20 to 50 degrees and is angled to allow the upright 40 to remain clear of the patient's ankle joint. Each post 40, 46 also has a second linear portion (or substantially linear portion) 86, 88 which are preferably substantially vertical or parallel to a patient's leg.

Referring again to FIG. 1, a selectively detachable strap 90 is attached between attachment posts 40, 46. The strap 90 is attached preferably with a pivotable connection 92 to the posts 40, 46. The strap 90, when worn, rests in the vicinity of the neck and head of the patient's talus of the foot. Strap 90 applies a force vector represented by vector 93 that helps to hold second edge 62 of the U-shaped member 28 against lip 76. Strap 90 preferably a hook-and-loop attachment strap (e.g., Velcro®).

While the dimension of attachment device 26 may vary with patient and with the particular shoe 30 for which the device is to be applied as part of system 10, in one specific embodiment tested, the following dimensions (with reference to FIG. 3) were used: Dimension A was ⅝"; Dimension B was 2½"; and Dimension C was 2¹⁵⁄₁₆". The thickness of U-shaped member 28 was ³⁄₃₂".

Figure 5:
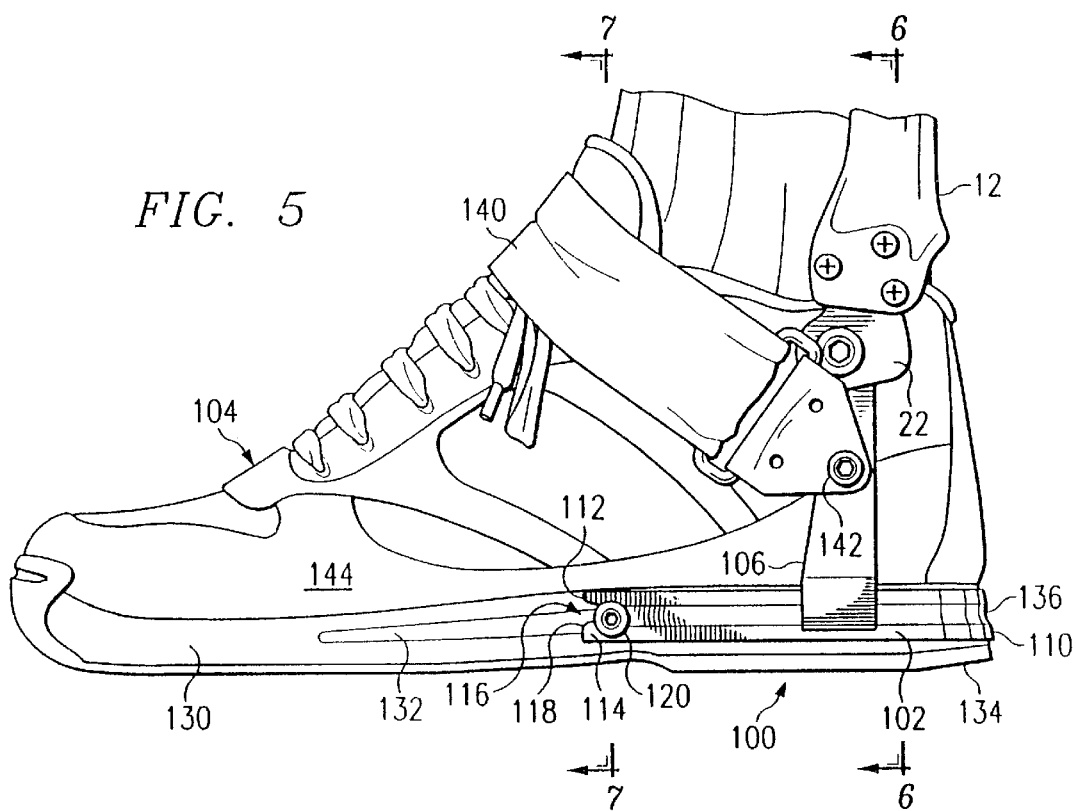
FIG. 5 is a side elevational skematic drawing of another embodiment of an ankle-orthosis system.
Figure 6:
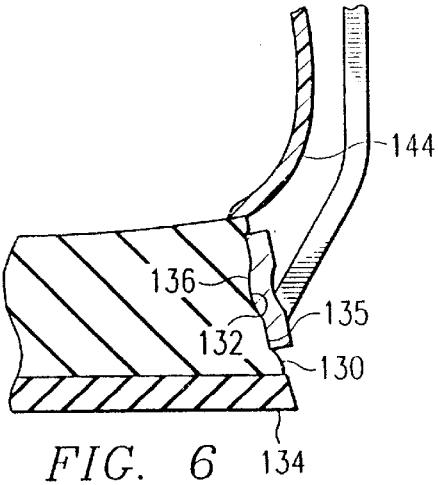
FIG. 6 is a partial cross-sectional view taken along line 6—6 of FIG. 5.
Figure 7:
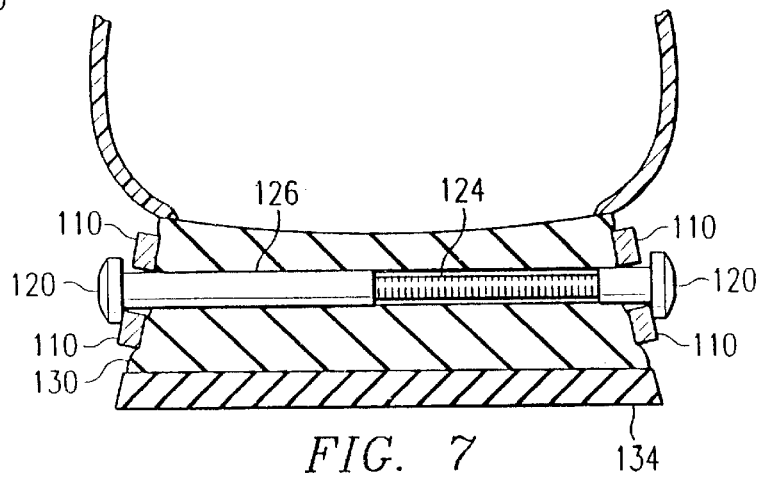
FIG. 7 is a partial cross-sectional view taken along line 7—7 of FIG. 5.

Referring now to FIGS. 5–7, another system and method are described. Ankle-foot orthosis system 100 uses an upper post member and calf band analogous to those shown in FIGS. 1 and 2, but utilizes another embodiment of an attachment device 102 and a different shoe design 104. The attachment device 102 has a first attachment post 106 and a second attachment post 108 (analogous to posts 40, 46). Posts 106, 108 are attached to a U-shaped member 110. On each end, such as end 112, is a channel and hook connection 114 formed by a channel 116 in the U-shaped member 110 and a hook 118. The channel and hook connection 114 is used to engage a flanged head 120 of a fastener 122 having a first half and a second half 126 (see FIG. 7).

Shoe 104 has sidewalls 130 that may be angled and are formed with a concave trough 132. The U-shaped member 110 is angled to be substantially coplanar with an exterior surface 135 of the heel portion 134 of shoe 104. Further, the U-shaped member 110 is formed with a convex portion 136 that mates with concave trough portion 132.

When in use by a patient, the attachment device 102 is placed with the U-shaped member 110 against the exterior surface 135 of heel 134 with convex member 136 engaging trough 132 of shoe 104. Channel and hook connection 114 is caused to engage the flanged heads 120 of fasteners 124, 126 to hold the U-shaped member in tension. This action secures the attachment device 102 to shoe 104. To further secure and stabilize attachment device 102, a selectively detachable strap 140 may be attached by pivot connections 142 to post members 106, 108. Strap 140 functions analogously to strap 90 (FIG. 1). Strap 140 may rest over a portion of the shoe outer 144.

Although the present invention and its advantages have been described in detail, it should be understood that various changes, substitutions and alterations can be made therein without departing from the spirit and scope of invention as defined by the appended claims.

What is claimed is:

1. An ankle-foot orthosis (A.F.O.) system for controlling the alignment and motions of the joints of the foot and ankle of a patient, the system comprising:
    an upper post member having a first end and a second end;
    a calf connection means for connecting the second end of the upper post to a patient's leg;
    a shoe having a sole side wall with a heel portion that has an exterior angled surface that is angled with respect to a vertical reference and at least a portion of the side wall; and
    a shoe-attachment device for attaching to the shoe and pivotably coupling to the first end of the upper post member, the attachment device comprising:
        an inwardly angled, u-shaped member having a first edge and a second edge and an interior surface, the angled, u-shaped member sized and formed to have the interior surface substantially co-planar with an exterior angled surface of the heel portion of the sole side wall of the shoe,
        a first attachment post having a first end and a second end, the first end of the first attachment post rigidly attached to the u-shaped member, the second end of the attachment post having a first pivot connection member,
        a second attachment post having first end and second end, the first end of the second attachment post rigidly attached to the u-shaped member approximately aligned with the first attachment post member, the second end of the second attachment post having a a second pivot connection member, and
        a selectively detachable strap secured with a pivotable connection to the first attachment post and with a pivotable connection to the second attachment post.

2. The system of claim 1 wherein the shoe further comprises an engageable lip formed between the exterior angled surface and an outer portion of the shoe, and wherein:
    the angled, u-shaped member is formed with an edge to engage the engageable lip of the shoe; and
    wherein the selectively detachable strap and angled, u-shaped member are formed such that when in use the strap places the u-shaped member in tension and urges the edge of the angled, u-shaped member into the engageable lip.

3. A method for manufacturing a system for helping to control the alignment and motions of foot and ankle joints of a patient, the method comprising the steps of:
    providing an upper post member having a first end and a second end;
    attaching a calf connection strap to the post member for connecting the second end of the upper post to a patient's leg;
    providing a shoe having a sole side wall with a heel portion that has an exterior angled surface that is angled with respect to a vertical reference;
    providing a shoe attachment device, wherein this step further comprises:
        forming an angled, u-shaped member having a first edge and a second edge and an interior surface, the angled, u-shaped member sized and configured so that the interior surface is substantially co-planar with an exterior angled surface of the heel portion of the sole side wall of the shoe when the attachment device is placed on the shoe,
        forming a first attachment post having a first end and a second end,
        attaching the first end of the first attachment post to the u-shaped member,
        attaching a first pivot connection member to the second end of the attachment post,
        attaching a second attachment post to the U-shaped member, the post having first end and second end,
        attaching a second pivot connection to the the second end of the second attachment post, and
        attaching a selectively detachable strap with a pivotable connection to the first attachment post and with a pivotable connection to the second attachment post;
    pivotally coupling the shoe-attachment device to the first end of the upper post member; and
    attaching the shoe-attachment device to the patient's shoe.

* * * * *